(12) United States Patent
Bickford et al.

(10) Patent No.: US 8,700,550 B1
(45) Date of Patent: *Apr. 15, 2014

(54) ADAPTIVE MODEL TRAINING SYSTEM AND METHOD

(75) Inventors: Randall L. Bickford, Orangevale, CA (US); Rahul M. Palnitkar, Lincoln, CA (US); Vo Lee, Elk Grove, CA (US)

(73) Assignee: Intellectual Assets LLC, Lake Tahoe, NV (US)

( * ) Notice: Subject to any disclaimer, the term of this patent is extended or adjusted under 35 U.S.C. 154(b) by 410 days.

This patent is subject to a terminal disclaimer.

(21) Appl. No.: 12/798,152

(22) Filed: Mar. 29, 2010

Related U.S. Application Data

(63) Continuation-in-part of application No. 12/315,118, filed on Nov. 28, 2008, now Pat. No. 8,145,444.

(60) Provisional application No. 61/005,056, filed on Nov. 30, 2007.

(51) Int. Cl.

| | | |
|---|---|---|
| *G06F 15/18* | (2006.01) | |
| *G06N 99/00* | (2010.01) | |
| *G06N 3/00* | (2006.01) | |
| *G01N 21/27* | (2006.01) | |
| *G01R 35/00* | (2006.01) | |
| *G06Q 50/06* | (2012.01) | |
| *H02J 3/00* | (2006.01) | |
| *G01D 18/00* | (2006.01) | |
| *G01D 21/00* | (2006.01) | |
| *G01P 21/00* | (2006.01) | |
| *G05D 3/12* | (2006.01) | |
| *G05D 5/00* | (2006.01) | |
| *G05D 9/00* | (2006.01) | |

(52) U.S. Cl.
CPC .............. *G06N 99/005* (2013.01); *G06N 3/004* (2013.01); *G01N 21/274* (2013.01); *G01R 35/005* (2013.01); *G06Q 50/06* (2013.01); *H02J 3/00* (2013.01)
USPC ................................ 706/14; 702/85; 700/286

(58) Field of Classification Search
CPC ... G06N 99/005; G06N 3/004; G01N 21/274; G01R 35/005; G06Q 50/06; H02J 3/00
USPC ................................ 706/14; 702/85; 700/286
See application file for complete search history.

(56) References Cited

U.S. PATENT DOCUMENTS

| | | |
|---|---|---|
| 5,223,207 A | 6/1993 | Gross et al. |
| 5,351,200 A | 9/1994 | Impink et al. |

(Continued)

OTHER PUBLICATIONS

Bickford, Randall, and Donald Malloy. "Development of a real-time turbine engine diagnostic system." Proceedings of the 38th AIAA/ASME/SAE/ASEE Joint Propulsion Conference, Indiana. 2002.*

(Continued)

*Primary Examiner* — Jeffrey A Gaffin
*Assistant Examiner* — James F Sugent
(74) *Attorney, Agent, or Firm* — Dennis A. DeBoo

(57) ABSTRACT

An adaptive model training system and method for filtering asset operating data values acquired from a monitored asset for selectively choosing asset operating data values that meet at least one predefined criterion of good data quality while rejecting asset operating data values that fail to meet at least the one predefined criterion of good data quality; and recalibrating a previously trained or calibrated model having a learned scope of normal operation of the asset by utilizing the asset operating data values that meet at least the one predefined criterion of good data quality for adjusting the learned scope of normal operation of the asset for defining a recalibrated model having the adjusted learned scope of normal operation of the asset.

15 Claims, 12 Drawing Sheets

(56) References Cited

U.S. PATENT DOCUMENTS

| | | | |
|---|---|---|---|
| 5,410,492 | A | 4/1995 | Gross et al. |
| 5,459,675 | A | 10/1995 | Gross et al. |
| 5,506,794 | A | 4/1996 | Lange et al. |
| 5,764,509 | A | 6/1998 | Gross et al. |
| 6,049,578 | A | 4/2000 | Senechal et al. |
| 6,067,505 | A | 5/2000 | Bonoyer et al. |
| 6,119,111 | A | 9/2000 | Gross et al. |
| 6,131,076 | A | 10/2000 | Stephan et al. |
| 6,442,542 | B1 | 8/2002 | Ramani et al. |
| 6,446,027 | B1 | 9/2002 | O'Keeffe et al. |
| 6,487,459 | B1 | 11/2002 | Martin et al. |
| 6,609,036 | B1 | 8/2003 | Bickford |
| 6,892,163 | B1* | 5/2005 | Herzog et al. ............... 702/181 |
| 6,898,469 | B2 | 5/2005 | Bickford |
| 6,917,839 | B2 | 7/2005 | Bickford |
| 6,975,962 | B2 | 12/2005 | Wegerich et al. |
| 7,039,554 | B2 | 5/2006 | Nguyen et al. |
| 7,082,379 | B1 | 7/2006 | Bickford et al. |
| 7,158,917 | B1 | 1/2007 | Bickford |
| 7,233,886 | B2 | 6/2007 | Wegerich et al. |
| 7,275,018 | B2 | 9/2007 | Abu-El-Zeet et al. |
| 7,415,382 | B1 | 8/2008 | Bickford et al. |
| 8,145,444 | B1* | 3/2012 | Bickford et al. ............... 702/85 |
| 2003/0055607 | A1 | 3/2003 | Wegerich et al. |
| 2004/0204908 | A1 | 10/2004 | Hosaka et al. |
| 2005/0007249 | A1 | 1/2005 | Eryurek et al. |
| 2005/0068446 | A1 | 3/2005 | Steinburg et al. |
| 2006/0178762 | A1* | 8/2006 | Wroblewski et al. ........... 700/30 |
| 2006/0273896 | A1 | 12/2006 | Kates |
| 2007/0038838 | A1 | 2/2007 | Greis et al. |

OTHER PUBLICATIONS

Willsky, A.S, A Survey of Design Methods for Failure Detection in Dynamic Systems, Automatica, vol. 12, pp. 601-611, Printed in Great Britain, 1976 (Year of publication is sufficiently earlier than the effective U.S. filing date and any foreign priority date so that the particular month of publication is not an issue).

S. Zacks, Sequential Testing and Confidence Intervals for the MTBF of Systems having Exponential Distribution of the Interfailure Times, Report No. GWU/IMSE/Serial_T-506/85, George Washington University, Dec. 23, 1985, Entire Report & Appendix pp. 1-23.

P.M. Frank, Fault Diagnosis in Dynamic Systems Via State Estimation, University of Duisburg, Department of Electrical Engineering Measurement and Control, Paper, pp. 35-85, Federal Republic of Germany, 1986 (Year of publication is sufficiently earlier than the effective U.S. filed and any foreign priority date so that the particular month of publication is not an issue).

Gross, K.C., et al, Sequential Probability Ratio Test for Nuclear Plant Component Surveillance, Nuclear Technology, vol. 93, pp. 131-137, Feb. 1991.

Singer, R.M., et al, A Pattern-recognition-based, Fault-tolerant Monitoring and Diagnostic Technique, 7th Symposium on Nuclear Reactor Surveillance, Jun. 1995, Entire Document, pp. 1-12, Printed in USA by Argonne National Laboratory.

A. Racz, Comments on the Sequential Probability Ratio Testing Methods, Annals of Nuclear Energy, vol. 23, No. 11, pp. 919-934, 1996. (Year of publication is sufficiently earlier than the effective US filing date and any foreign priority date so that the particular month of publication is not an issue).

K. Kulacsy,Further Comments on the Sequential Probability Ratio Testing Methods,prepared for Annals of Nuclear Energy by the KFKI Atomic Energy Research Institute,Budapest, Hungary,Report No. KFKI-1996-10/G, pp. 1-9, 1996(Year of publication is sufficiently earlier than effective US filing date and any foreign priority date so that particular month of publication is not an issue).

Bickford, R.L., et al, Real-Time Flight Data Validation for Rocket Engines, American Institute of Aeronautics and Astronautics, Inc., 1996, pp. 1-8, Printed in USA by ExperTech & NYMA, Inc. (Year of publication is sufficiently earlier than the effective U.S. filing date and any foreign priority date so that the particular month of publication is not an issue).

Wrest, D.J., et al., Instrument Surveillance and Calibration Verification through Plant Wide Monitoring Using Autoassociative Neural Networks, Specialists Meeting on Monitoring and Diagnosis Systems to Improve Nuclear Power Plant Reliability and Safety, U.K., May 1996, pp. 1-16, printed by the International Atomic Energy Agency.

R. M. Singer, et al, Model-Based Nuclear Power Plant Monitoring and Fault Detection: Theoretical Foundations, Proceedings. 9th International Conference on Intelligent Systems Applications to Power Systems, Seoul, Korea, Jul. 6-10, 1997, pp. 60-65.

Gross, K.C., et al, Application of a Model-based Fault Detection System to Nuclear Plant Signals, Proceedings 9th International Conference on Intelligent Systems Applications to Power Systems, Seoul, Korea, Entire Document, pp. 1-5, May 1, 1997.

Bickford, R.L., et al, Real-Time Sensor Validation for Autonomous Flight Control, American Institute of Aeronautics and Astronautics, Printed in USA by Expert Microsystems, Inc. & Intelligent Software Associates, Inc. & Boeing Defense and Space Group, Entire Document, pp. 1-11, Jul. 1997.

Singer, R.M., et al, Power Plant Surveillance and Fault Detection: Applications to a Commercial PWR, International Atomic Energy Agency, IAEA-TECDOC-1054, pp. 185-200, Sep. 1997.

Kulacsy, K., Tests of the Bayesian Evaluation of SPRT Outcomes on PAKS NPP Data, KFKI Atomic Energy Research Institute, Budapest, Hungary, Report No. KFKI-1997-07/G, Dec. 1997, Entire Document, pp. 1-21.

Herzog, J.P., et al, Dynamics Sensor Validation for Reusable Launch Vehicle Propulsion, AIAA 98-3604, 34th Joint Propulsion Conference, Cleveland, Ohio, Jul. 13, 1998, Entire Document, pp. 1-12.

Bickford, R.L., et al, Real-Time Sensor Validation For Propulsion Systems, American Institute of Aeronautics and Astronautics, Printed in USA by Expert Microsystems, Inc & Dynacs Engineering Co. pp. 1-7, 1998, (Year of publication is sufficiently earlier than the effective U.S. filing date and any foreign priority date so that the particular month of publication is not an issue).

Herzog, J.P., et al, MSET Modeling of Crystal River-3 Venturi Flow Meters, 6th International Conference on Nuclear Engineering, May 1998, Printed in USA by ASME, Entire Document—pp. 1-17.

Bickford, R.L., et al, Real-Time Sensor Data Validation for Space Shuttle Main Engine Telemetry Monitoring, AIAA, Jun. 1999, Printed in USA by Expert Microsystems, Inc.& Intelligent Software Associates, Inc. & Dynacs Engineering Company & NASA Glenn Research Center, Entire Document—pp. 1-9.

Yamanishi, K., et al, On-line unsupervised outlier detection using finite mixtures with discounting learning algorithms. In Proceedings of the Sixth ACM SIGKDD International Conference on Knowledge Discovery and Data Mining, pp. 320-324, Boston, MA, USA, Aug. 20-23, 2000.

Zavaljevski, N., et al, Support Vector Machines for Nuclear Reactor State Estimation, ANS Topical Mtg. on Advances in Reactor Physics, May 2000, Printed in USA by Argonne National Laboratory, Entire Document—pp. 1-14.

Wegerich, S., et al, Challenges Facing Equipment Condition Monitoring Systems, MARCOM 2001, May 2001, Printed in USA by SmartSignal Corporation, pp. 1-11.

Bickford, R.L., et al, Online Signal Validation for Assured Data Integrity, 47th International Instrumentation Symposium, May 2001, Printed in USA by Expert Microsystems, Inc., and NASA Glenn Research Center, pp. 1-10.

Litt, J.S., et al, A Survey of Intelligent Control and Health Management Technologies for Aircraft Propulsion Systems, NASA Glenn Research Center, Report No. NASA/TM-2005-213622, May 2005, Entire document—pp. 1-24.

Bickford, R.L., et al, Ground Test Facility Implementation of a Real-Time Turbine Engine Diagnostic System, American Institute of Aeronautics and Astronautics (AIAA), 41st Joint Propulsion Conference, Jul. 2005, Printed in USA by AIAA, Entire document—pp. 1-11.

Chen, H., et al, Failure Detection and Localization in Component Based Systems by Online Tracking, NEC Laboratories America, 11th. ACM SIGKDD International Conference on Knowledge Discovery in Data Mining, pp. 750-755, Aug. 2005.

(56) References Cited

OTHER PUBLICATIONS

Spitzlsperger, G., et al, Fault Detection for a Via Etch Process Using Adaptive Multivariate Methods, In IEEE Transactions on Semiconductor Manufacturing, vol. 18, No. 4, pp. 528-533, Nov. 2005.

Bickford, R.L., et al, Ground Test Data Validation Using a Subscale F/A-22 Engine Inlet Empirical Model, In Proceedings of GT2006, ASME Turbo Expo 2006: Power, for Land, Sea, and Air, May 2006, Barcelona, Spain, Entire document—pp. 1-15.

* cited by examiner

A computer-implemented adaptive model training method, said method comprising the steps of:

↓

Acquiring asset operating data values from monitoring an asset;

↓

Filtering the acquired asset operating data values for selectively choosing asset operating data values that meet at least one predefined criterion of good data quality while rejecting asset operating data values that fail to meet at least the one predefined criterion of good data quality; and

↓

Recalibrating a trained model having a learned scope of normal operation of the asset by utilizing the asset operating data values that meet at least the one predefined criterion of good data quality for adjusting the learned scope of normal operation of the asset for defining a recalibrated model having the adjusted learned scope of normal operation of the asset for subsequent use in monitoring the asset.

FIG. 2

```
┌─────────────────────────────────────────────────────┐
│ A recursive, computer-implemented adaptive model    │
│ training method of at least one model utilized for  │
│ monitoring of at least one asset, said method       │
│ comprising the steps of:                            │
└─────────────────────────────────────────────────────┘
                          ↓
┌─────────────────────────────────────────────────────┐
│ Dynamically filtering asset operating data values   │
│ acquired during asset monitoring or a transformation│
│ of the asset operating data values to separate good │
│ data, which can be used for adaptive model training,│─┐
│ from bad data, which should not be used for adaptive│ │
│ model training;                                     │ │
└─────────────────────────────────────────────────────┘ │
                          ↓                             │
┌─────────────────────────────────────────────────────┐ │
│ Combining the newly acquired good data with good    │ │
│ data previously acquired and previously used for a  │ │
│ prior model training step and optionally reducing   │ │
│ the size of the combined set of data to the size of │ │
│ the data stored from the prior model training step; │ │
│ and                                                 │ │
└─────────────────────────────────────────────────────┘ │
                          ↓                             │
┌──────────────────────────┐                            │
│ Recalibrating the        │              Yes           │
│ monitoring model         │         ╱╲                 │
│ elements using the       │        ╱  ╲                │
│ newly combined and       │──────▶╱Recal-╲─────────────┘
│ optionally reduced good  │       ╲ibrate?╱
│ data, periodically or on │        ╲    ╱
│ user demand;             │         ╲  ╱
└──────────────────────────┘          ╲╱
                                       │ No
                                       ↓
                              ┌──────────────────┐
                              │ End Recalibration.│
                              └──────────────────┘
```

FIG. 5

| Similarity Calculation for Ordering | Anderson Darling | | | Chi Squared | | |
|---|---|---|---|---|---|---|
| | Mean RMS Error % | Std Dev of RMS Error % | Number of Clusters | Mean RMS Error % | Std Dev of RMS Error % | Number of Clusters |
| Level Example: 4 signals, 125 Vectors selected, 2998 training data points (TDPs) | | | | | | |
| Similarity Angle | 0.02066 | 0.004391 | 1 | 0.02066 | 0.004391 | 1 |
| Anderson-Darling | 0.02342 | 0.005743 | 1 | 0.02342 | 0.005743 | 1 |
| Euclidian Distance | 0.02043 | 0.004007 | NA | NA | NA | NA |
| NO_PHASES Typical Steam System: 36 Signals, 72 Points Selected, 2998 TDPs | | | | | | |
| Similarity Angle | 0.1795 | 0.1744 | 3 | 0.1795 | 0.1744 | 3 |
| Anderson-Darling | 0.1767 | 0.1702 | 3 | 0.1767 | 0.1702 | 3 |
| Euclidian Distance | 0.2314 | 0.2286 | NA | NA | NA | NA |
| HHLC_MIN : 18 signals, 58 Vectors Selected, Training Data; 40,000 data points | | | | | | |
| Similarity Angle | 3.0162 | 0.9785 | 13 | 3.0296 | 0.9768 | 12 |
| Anderson-Darling | 2.9951 | 0.9558 | 13 | 3.0746 | 1.0815 | 13 |
| Euclidian Distance | 3.2294 | 1.0979 | NA | NA | NA | NA |
| NO_PHASES_SSME: 5 Signals, 394 Vectors Selected, 09p1.025: 40,000 data points | | | | | | |
| Similarity Angle | 0.23 | 0.05643 | 216 | 0.2028 | 0.05172 | 167 |
| Anderson-Darling | 0.115 | 0.03134 | 216 | 0.1425 | 0.04122 | 167 |
| Euclidian Distance | 1.9867 | 0.4721 | NA | NA | NA | NA |
| Grid: 2 signals, 100 Points Selected, Training Data: 2500 data points | | | | | | |
| Similarity Angle | 0.2252 | 0.0739 | 4 | 0.2055 | 0.04964 | 1 |
| Anderson-Darling | 0.1994 | 0.02645 | 4 | 0.2326 | 0.03097 | 1 |
| Euclidian Distance | 2.2209 | 0.02288 | NA | NA | NA | NA |

FIG. 6

| SIGNAL | DESCRIPTION | UNITS |
|---|---|---|
| CP-01 | STEAM GENERATOR A NR LEVEL(LT474) | PCT |
| CP-02 | STEAM GENERATOR A NR LEVEL(LT475) | PCT |
| CP-03 | STEAM GENERATOR A NR LEVEL(LT476) | PCT |
| CP-04 | STEAM GENERATOR A WR LEVEL(LT477) | PCT |

FIG. 9

ADAPTIVE MODEL TRAINING SYSTEM AND METHOD

CROSS-REFERENCE TO RELATED APPLICATIONS

This application is a continuation-in-part patent application of U.S. application Ser. No. 12/315,118, filed Nov. 28, 2008, now U.S. Pat. No. 8,145,444, and which claims priority to U.S. Provisional Patent Application No. 61/005,056, filed Nov. 30, 2007, both disclosures of which are incorporated herein by reference in their entireties.

This application is also related to and is being filed concurrently with U.S. application Ser. No. 12/798,128, and entitled "Dynamic Data Filtering System and Method,", the entire disclosure of which is incorporated by reference herein in its entirety.

STATEMENT REGARDING FEDERALLY SPONSORED RESEARCH AND DEVELOPMENT

This invention was made with Government support under Small Business Innovation Research (SBIR) Grant No. DE-FG02-04ER83949 awarded by the United States Department of Energy. The Government has certain rights in the invention. This invention is subject to the provisions of Public Law 96-517 (35 USC 202) and the Code of Federal Regulations 48 CFR 52.227-11, in which the contractor has elected to retain title.

FIELD OF THE INVENTION

This invention relates generally to model training and, in particular, to an adaptive model training system and method for adaptively calibrating at least one model representative of normal operation of at least one monitored asset for, but not limited to, utilization in an adaptive on-line monitoring system and method for productive assets, such as, but not limited to power plant equipment.

BACKGROUND OF THE INVENTION

To assure the continued safe, reliable and efficient operation of a power plant, it is essential that accurate on-line information about the current state of the equipment be available to the operators. Such information is needed to determine the operability of safety and control systems, the condition of active equipment, the necessity of preventive maintenance, and the status of sensory systems.

Products useful for determining or monitoring the condition or remaining useful life of productive assets, including but not limited to power plant equipment, most often perform this surveillance function by evaluating signal or data values obtained during asset operation. One means for determining or monitoring the condition of an asset involves estimating the expected data values and comparing the estimated values to current data values obtained from the asset. When the estimated data values characterize the desired or expected operation of the asset, a disagreement between the estimated data values and the current data values provides a sensitive and reliable indication of an asset degradation or fault condition and can further provide an indication of the particular cause and severity of the asset degradation or fault. The disagreement between each estimated data value and each current data value can be computed as the numerical difference between them. This difference is often referred to as a residual data value. The residual data values, the current data values, or the estimated data values can be used to determine condition of the asset and to identify or diagnose asset degradation or fault conditions.

One means for estimating the expected data values used for determining or monitoring the condition of an asset involves the use of machine learning to calibrate (train) a model representative of the normal operation of the monitored asset. A shortcoming in the prior application of machine learning is the need to calibrate or train the model of normal operation prior to its use for on-line monitoring. The calibrated model then remains static during on-line monitoring operations. Often, asset aging changes or operating condition changes cause a statically calibrated model to eventually estimate poorly the expected data values. When the poorly estimated expected data values are then compared to current data values obtained from the asset during on-line monitoring, false alarms typically result. Currently, this problem plagues all known power industry deployments of empirical models developed by machine learning and used to determine condition of an asset or to identify or diagnose asset degradation or fault conditions over any substantial period of monitoring.

For the foregoing reasons, there is a need to overcome the significant shortcomings of the known prior-art as delineated hereinabove.

BRIEF SUMMARY OF THE INVENTION

Accordingly, and in one aspect, an embodiment of the invention ameliorates or overcomes one or more of the significant shortcomings of the known prior art by providing an adaptive model training system and method for adaptively calibrating at least one model representative of normal operation of at least one monitored asset for, but not limited to, providing an adaptive on-line monitoring system and method for productive assets, such as, but not limited to power plant equipment.

In one aspect, an embodiment of the adaptive model training method comprises the steps of selectively calibrating a model having a learned scope of normal asset operation by utilizing asset operating data acquired from an asset that modifies or expands the learned scope of normal asset operation of the model while simultaneously rejecting asset operating data that is indicative of abnormal operation of the asset, such as excessive degradation or impending failure of the asset to perform its service requirements, from inclusion in the calibration process.

This adaptive calibration of the model by machine learning provides for optimization and deployment of effective on-line condition monitoring systems for a wide variety of, for example, power plant assets.

In a further aspect, an embodiment of the adaptive model training system and method provides adaptive recalibration of a model having a learned scope of normal operation of an asset during on-line operation.

In a further aspect, an embodiment of the adaptive model training system and method is suitable for use where empirical models need to be recalibrated dynamically without manual intervention.

In a further aspect, an embodiment of the adaptive model training system and method is suitable for, but not limited to, use with an on-line system monitoring power plant equipment.

In a further aspect, an embodiment of the adaptive model training system and method is suitable for a variety of empirical models types.

In a further aspect, an embodiment of the invention provides a computer-implemented adaptive model training method, said method comprising the steps of: filtering asset operating data values acquired from an asset for selectively choosing asset operating data values that meet at least one predefined criterion of good data quality while rejecting asset operating data values that fail to meet at least the one predefined criterion of good data quality; and recalibrating a previously trained model having a learned scope of normal operation of the asset by utilizing the asset operating data values that meet at least the one predefined criterion of good data quality for adjusting the learned scope of normal operation of the asset for defining a recalibrated model having the adjusted learned scope of normal operation of the asset. Additionally, an embodiment of the invention provides a non-transitory computer-readable medium containing computer-executable instructions that, when executed by a processor, cause the processor to perform the above adaptive model training method. Furthermore, an embodiment of the invention provides a system comprised of means for accomplishing the functions of the steps of the above adaptive model training method.

In a further aspect, an embodiment of the invention provides a computer-implemented adaptive model training method, said method comprising the steps of: filtering asset operating data values acquired from an asset for selectively choosing asset operating data values that meet at least one predefined criterion of good data quality while rejecting asset operating data values that fail to meet at least the one predefined criterion of good data quality; combining training data values that have been used previously for prior model training with the acquired asset operating data values that meet at least the one predefined criterion of good data quality for defining a combined set of data values; and recalibrating a previously trained model having a learned scope of normal operation of the asset by utilizing at least a portion of the combined set of data values for adjusting the learned scope of normal operation of the asset for defining a recalibrated model having the adjusted learned scope of normal operation of the asset. Additionally, an embodiment of the invention provides a non-transitory computer-readable medium containing computer-executable instructions that, when executed by a processor, cause the processor to perform the above adaptive model training method. Furthermore, an embodiment of the invention provides a system comprised of means for accomplishing the functions of the steps of the above adaptive model training method.

Accordingly, it should be apparent that numerous modifications and adaptations may be resorted to without departing from the scope and fair meaning of the claims as set forth herein below following the detailed description of the invention.

BRIEF DESCRIPTION OF THE DRAWINGS

FIG. 2 is a functional flow diagram of an embodiment of a computer-implemented adaptive model training procedure or method.

FIG. 5 is a functional flow diagram of an embodiment of a recursive, computer-implemented adaptive model training method of at least one model utilized for monitoring of at least one asset.

FIG. 6 illustrates a comparison table of clustering method test statistics.

FIG. 9 is a table illustrating signals incorporated into a model of feedwater levels of a steam generator in an operating nuclear power plant.

DETAILED DESCRIPTION OF THE INVENTION

Figure 1:
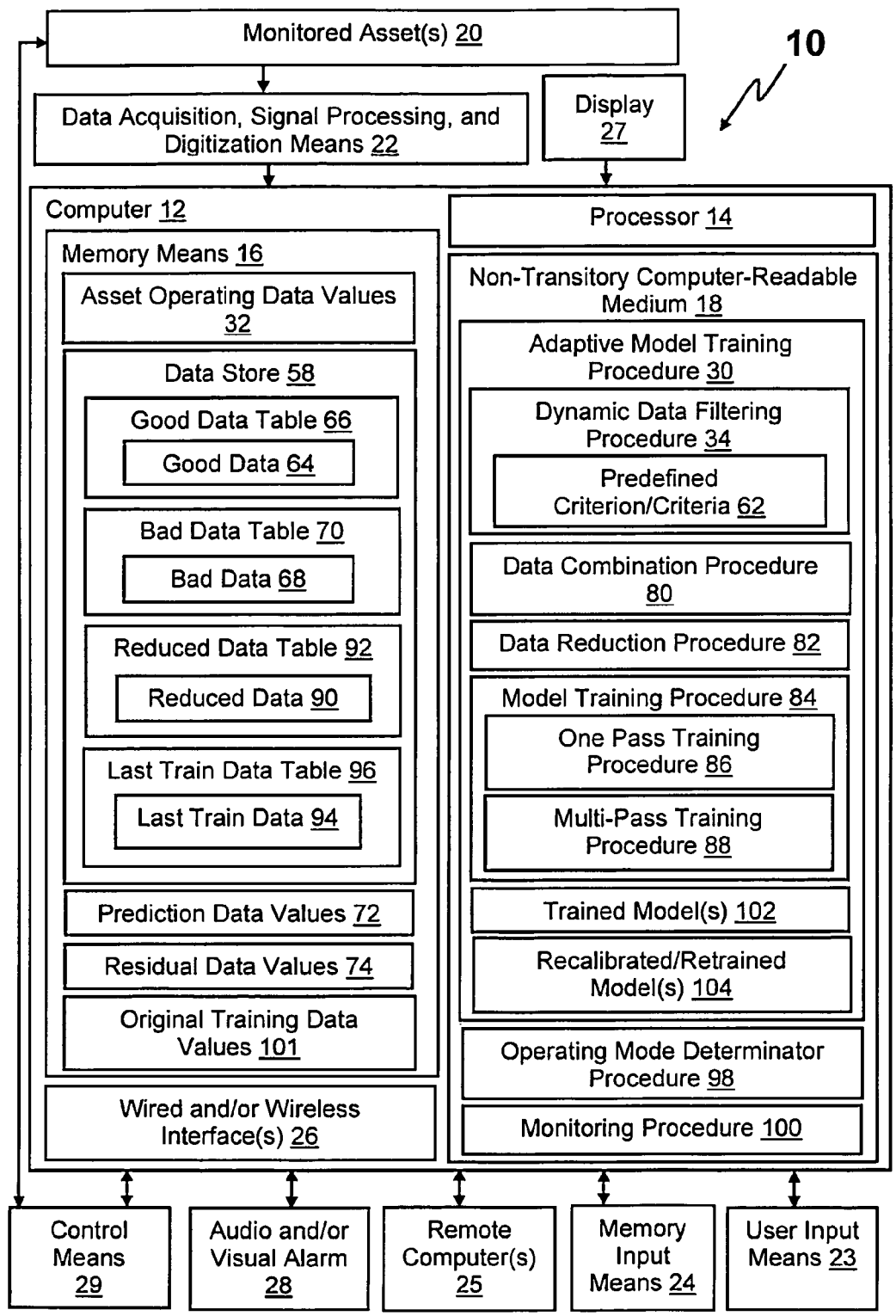
FIG. 1 is a functional block diagram of an embodiment of an adaptive model training system and method.

Considering the drawings, wherein like reference numerals denote like parts throughout the various drawing figures, reference numeral 10 is directed to an adaptive model training system and method for adaptively calibrating at least one model representative of normal operation of at least one monitored asset.

Referring to FIG. 1, and in one embodiment, the adaptive model training system and method 10 is comprised of a computer 12 having a processor 14, memory means 16, and a non-transitory computer-readable medium 18 storing an adaptive model training procedure or method 30 comprised of computer-executable instructions that, when executed by the processor 14, cause the processor 14 to perform the adaptive model training method 30, the method comprising the steps of: acquiring on-line or in a consecutive order asset operating data values 32 from monitoring results of a monitored asset 20; determining data quality for each of the acquired asset operating data values 32 and saving acquired asset operating data values 32 having good quality for defining good quality data 64; and utilizing the good quality data 64 for adaptive calibration of a model 102 by machine learning for defining a recalibrated model 104.

In one embodiment, the step of utilizing the good quality data 64 for adaptive calibration of the empirical model 102 by machine learning includes recalibrating prediction models, fault detection models, dynamic data filter models, and/or other on-line monitoring system elements. Additionally, and in one embodiment, the steps of acquiring, filtering, and recalibrating are recursively performed periodically or on user demand. Furthermore, and in one embodiment, the adaptive model training method 30 is utilized in an on-line monitoring procedure 100 of productive assets, such as, but not limited to power plant equipment.

The acquisition of the observations of asset operating data values or observed data values 32 from at least one monitored asset 20 can be provided by a data acquisition, signal processing, and digitization means 22 electrically coupled between the computer 12 and at least the one monitored asset 20. The observations of asset operating data or observed data values 32 can also be acquired by the computer 12 via, for example, user input means 23, memory input means 24, and/or remote computer means 25 via a wired and/or wireless interface 26.

The determined or monitored condition of at least the one monitored asset 20 might be reported to a display 27 or to the remote computer 25 via the wired and/or wireless interface 26 and the predefined condition or fault reporting might be used to effect an alarm via an alarm means 28 or to effect a control action via an asset control means 29.

Non-transitory computer-readable medium 18 can include media such as magnetic media (such as hard disks, floppy disks, etc.), optical media (such as compact discs, digital video discs, Blu-ray discs, etc.), semiconductor media (such as non-volatile flash memory employed in, for example, Solid-state drive (SSD) devices, electrically programmable read only memory (EPROM), electrically erasable programmable read only memory (EEPROM), etc.), any suitable media that is not fleeting or devoid of any semblance of permanence during transmission, and/or any suitable tangible media. Additionally, non-transitory computer readable medium 18 may be employed for at least a portion of memory means 16. Furthermore, the non-transitory computer readable medium 18 and memory means 16 can be formed from one or more different types of media or memory.

Adaptive Model Training Procedure 30

The data used for the adaptive model training procedure 30 is obtained by dynamically filtering acquired data 32 with a dynamic data filtering procedure or method 34 during an on-line or periodic monitoring process 100. In one embodiment, each validated observation selected for the adaptive model retraining or recalibration process 30 must be determined to be of good quality. A determination of the goodness of the data is separate and distinct from the data validation and/or diagnostic monitoring processes typically performed during on-line or periodic monitoring process 100.

Accordingly, and referring to FIGS. 1 and 2, an embodiment of the adaptive model training system and method 10 is comprised of a computer-implemented adaptive model training method 30, the method comprising the steps of: acquiring asset operating data values 32 from monitoring results of the monitored asset 20; filtering the acquired asset operating data values 32 with dynamic data filtering procedure 34 for selectively choosing asset operating data values that meet at least one predefined criterion 62 of good data quality while rejecting asset operating data values 32 that fail to meet at least the one predefined criterion 62 of good data quality; and recalibrating the trained model 102 having a learned scope of normal operation of the asset by utilizing the asset operating data values 32 that meet at least the one predefined criterion 62 of good data quality for adjusting the learned scope of normal operation of the asset for defining the recalibrated model 104 having the adjusted learned scope of normal operation of the asset for subsequent use in monitoring the asset.

In another embodiment, the good data 64 will often be a combination of original training data 101 plus asset operating data values 32 that meet at least the one predefined criterion 62 and that are acquired during one or more adaptive training cycles wherein the combined good data is obtained by a combination procedure 80. A data reduction procedure 82 is performed during each adaptive training cycle to prevent the amount of good data 64 stored from becoming excessive. At least one model 102 or subsequently 104 is then retrained or recalibrated using the combined and reduced good data.

Hence, an embodiment of the adaptive model training procedure 30 is a process of recalibrating or retraining the model 102 or subsequently 104 over data that was acquired during monitoring.

Figure 3:
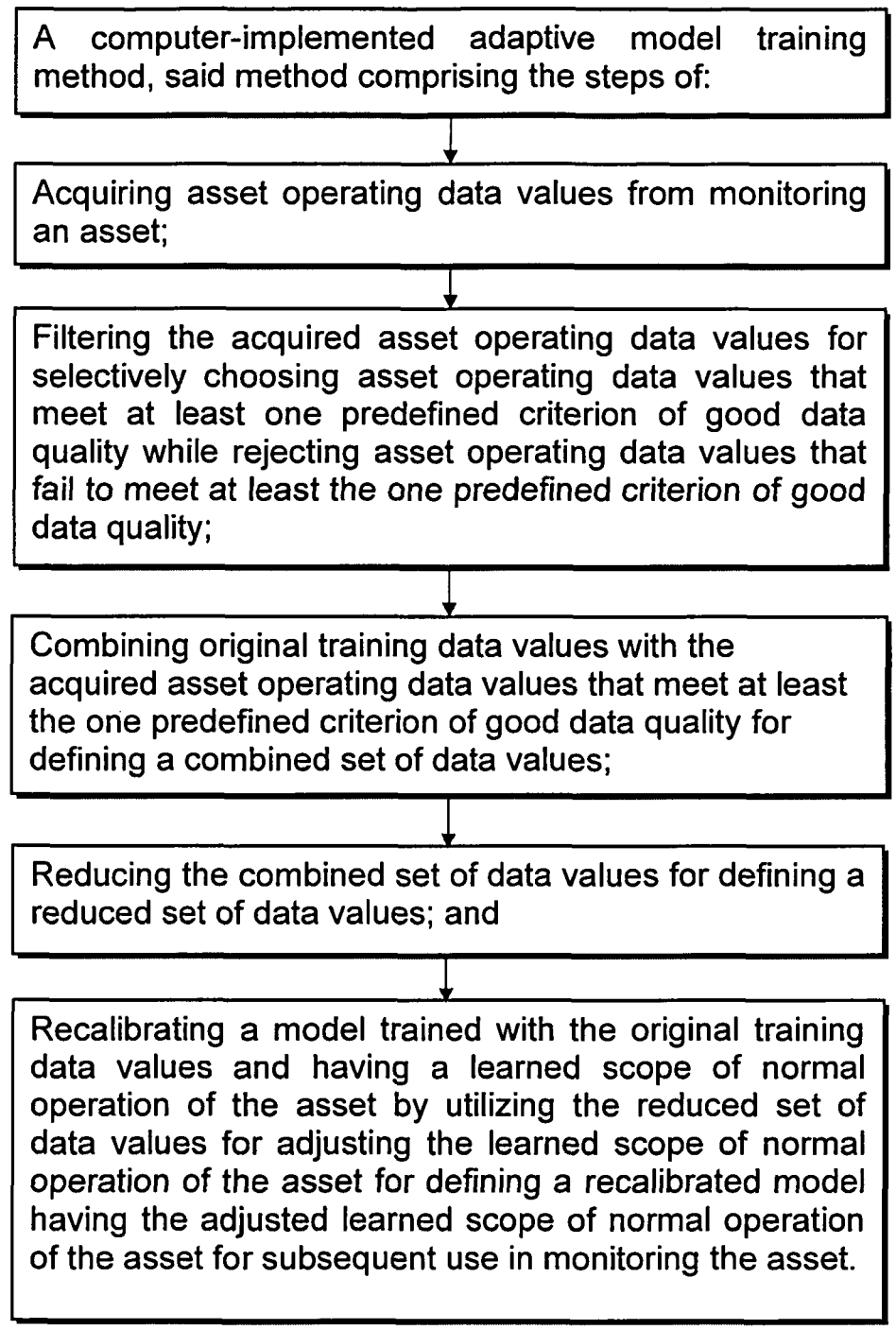
FIG. 3 is a functional flow diagram further detailing an embodiment of a computer-implemented adaptive model training procedure or method.

Accordingly, and referring to FIGS. 1 and 3, an embodiment the adaptive model training system and method 10 is comprised of a computer-implemented adaptive model training method 30, the method comprising the steps of: acquiring asset operating data values from the monitored asset 20; filtering the acquired asset operating data values with dynamic data filtering procedure 34 for selectively choosing asset operating data values 32 that meet at least one predefined criterion of good data quality while rejecting asset operating data values that fail to meet at least the one predefined criterion of good data quality; combining original training data values 101 with the acquired asset operating data values 32 that meet at least the one predefined criterion of good data quality for defining a combined set of good data values; reducing the combined set of data values for defining a reduced set of data values 92; and recalibrating the model 102 trained with the original training data values 101 and having a learned scope of normal operation of the asset by utilizing the reduced set of data values 92 for adjusting the learned scope of normal operation of the asset for defining the recalibrated model 104 having the adjusted learned scope of normal operation of the asset for subsequent use in monitoring the asset.

Detailed Adaptive Model Training Procedure 30

More specifically, and referring to FIGS. 4 and 5, an embodiment of the adaptive model training procedure 30 is implemented in a recursive process that can be delineated as having three main steps as follows:

Step One: Dynamic Data Filtering Method

The first main step of the adaptive model training procedure 30 is comprised of utilizing the dynamic data filtering procedure or method 34 as delineated in detail hereinbelow for performing a step of dynamically filtering asset operating or observed data values 32 acquired during an asset monitoring procedure 100, or a transformation of the asset operating data values, to separate good data 64, which can be used for adaptive model training, from bad data 68, which should not be used for adaptive model training. The data values can be comprised of asset operating or observed data values 32 and/or transformed data values in the form of, for example, prediction data values 72 and/or residual data values 74.

Additionally, the dynamic data filtering method 34 may further comprise an operating mode determinator procedure 98 for partitioning the data values into data subsets that identify periods of asset operation or operating modes wherein each of the data subsets is filtered to obtain good data 64 for use in the adaptive model training procedure 30.

Methods suitable for operating mode determinator procedure 98 include, but are not limited to, mathematical or logic sequence techniques, expert system techniques, a plurality of fuzzy logic techniques, determined similarity techniques, clustering techniques, and neural network techniques.

Operating mode partitioning systems and methods are described in U.S. Pat. No. 6,609,036; U.S. Pat. No. 6,898,469; U.S. Pat. No. 6,917,839; and U.S. Pat. No. 7,158,917 and which are all incorporated herein by reference in their entireties as though fully set forth herein and wherein each has a common inventor with the present application.

Step Two: Data Combination and Reduction

The second main step of the adaptive model training procedure 30 is comprised of utilizing a data combination procedure 80 for performing a step of combining the newly acquired good data 64 with good data previously acquired and previously used for a prior model training step (last train data 94 in the last train data table 96) and optionally utilizing the data reduction procedure 82 for reducing the size of the combined set of data to the size of the data stored from the prior model training step and storing this data as reduced data 90 in the reduced data table 92.

Step Three: Recalibrate/Retrain On-line Monitoring Model

The third main step of the adaptive model training procedure 30 is initiated periodically or on user demand during the monitoring procedure 100 of at least the one asset 20 and is comprised of elements of the on-line trained model 102 or the recalibrated or retrained model 104 being retrained or recalibrated on unreduced data obtained from the good data table 66 and the last train data table 96 and/or being retrained or recalibrated on reduced data 90 obtained from the reduced data table 92. After training is completed, the reduced data 90 becomes the new last train data 94 that will be used in the subsequent adaptive training cycle of procedure 30.

Many model element training processes are computationally intensive when performed over every observation. Hence, the adaptive model training procedure 30 obtains comparable results by utilizing a statistically similar subset of data, herein termed the reduced data 90. In one embodiment, a representative sample of the data can be obtained by first clustering the data and then selecting representative data from each cluster in proportions equal to their cluster size. In one embodiment, the data reduction procedure 82 was implemented as a "plug-in" so that different reduction methods might be substituted, depending on the goal of the reduction.

In one embodiment, the adaptive model training procedure 30 utilizes, but is not limited to, the following delineated data reduction procedure or method 82.

Mathematical Description of Data Reduction Method 82

In one embodiment of the instant invention, the data reduction procedure or method 82 is comprised of a modified G-Means Clustering Method combined with an ordering and selection method that is utilized to select a representative sample of data to accomplish data reduction. Variations of the technique were compared.

The data reduction procedure 82 implements a probability density function (PDF) model using similarity based clusters to partition the state space of the data. The objective is to divide the data into clusters with Gaussian distributions. The process is as follows: Initially define a cluster center to be a mean of the data; next, determine if the data has a Gaussian distribution around the center; then, if the distribution is Gaussian, there is one center and no further processing is required, but if the distribution is non-Gaussian, then define two clusters, assign each observation to one of the clusters and determine if they are both Gaussian; finally, repeat this process for all non-Gaussian clusters until all clusters have a Gaussian distribution or until a maximum number of clusters is reached. Details of how the distribution is known to be Gaussian, how new cluster centers are determined, and how individual observations are assigned to the clusters will now be delineated below in detail.

Determining a Cluster's Distribution

First, a distribution is Gaussian if its Anderson-Darling statistic is less than the critical value at confidence level, $1-\alpha$, which is specified by the user. The critical values may be found in the literature for specific confidence levels. Interpolation between confidence levels allows us to determine the critical value at confidence levels that fall between points.

The Anderson-Darling test statistic is calculated as follows:

Project Y onto:

$$v = c_1 - c_2$$

$$y'_i = <y_i, v>/\|v\|^2$$

Y' is a 1-dimensional representation of the subset of data projected on v.

Transform Y' so it has mean 0 and variance 1 (or z-scores Y').

Given a list of values $y_i$ that have been converted to mean 0 and variance 1, let y(i) be the ith ordered value. Let $$z_i = F(y'_i)$$

where F is the cumulative distribution function.

Calculate the test statistic as:

$$A^2(Z) = -\frac{1}{n}\sum_{i=1}^{n}(2i-1)[\ln(z_i) + \ln(1 - z_{n+1-i})] - n$$

For the case where the mean and the standard deviation are estimated from the data (as in clustering), $A^2(Z)$ must be corrected as:

$$A^2(Z) = A^2(Z)(1 + 4/n - 25/n^2)$$

If $A^2$ is larger than the critical value at the specified confidence level, then the distribution is Gaussian.

Determining New Cluster Centers

Once a cluster has been determined to be non-Gaussian, we split the cluster and establish two new centers as follows:

Initialize two centers in Y, called "children" of c, by finding the principal components (the eigenvector of the covariance matrix with the largest eigenvalue $\lambda$), and set them initially to:

$$c \pm \sqrt{2\lambda/\pi}$$

Assigning Individual Points to Each Cluster

A k-means clustering algorithm is used to cluster a set of n-element input vectors $\{X\}=\{x_i, \ldots, x_i, \ldots, x_n\}$ into k clusters, where n is the number of signals in each data observation. The k-means clustering algorithm proceeds as follows given an initial set of cluster centers.

Assign each input vector $x_i$ to the cluster $C_j$ with nearest centroid $w_j$.

For each cluster $C_j$ compute the centroid $w_j$ of all samples assigned to $C_j$. Compute the error function:

$$E = \sum_{j=1}^{k} \sum_{x_l \in C_j} |x_l - w_j|^2$$

Repeat k-means procedures 1 through 3 until E remains nearly constant or cluster membership does not change.

Two versions of this method were tested. The first used the Anderson Darling test statistic shown above. The second used the well known Chi-Squared test statistic to determine whether the distribution is Gaussian.

Ordering and Selection Method

Clustering of the data is followed by the selection of the representative vectors using a mixture model drawn from the vector similarity distributions present within each cluster. The fundamental improvement over the prior art vector ordering procedure is that this method selects the representative vectors using a similarity criterion whereas the prior art procedure selects the reference library vectors using a magnitude (distance from origin) criterion.

When selecting reference library vectors for a nonparametric kernel regression model, it is desirable to include the unique points that contain at least one of the minimum or maximum observation values (the so called minmax points) for each modeled parameter. Consequently, the clustering algorithm is run on the remaining observations after the selection of the minmax points.

Representative vectors are chosen from the mixture model by the selection of a number of fractiles from each cluster proportionate to the percentile of training data observations represented in the cluster (subject to a minimum) and sufficient to populate the user-specified reference library matrix size. To accomplish the selection, the points in each cluster are sorted by their computed similarity to the cluster center. Various similarity calculations were compared and only the technique providing the best results was ultimately implemented.

The method is performed as follows:

The points at one end of the sorted list are those that are most similar to the center with the most dissimilar points at the other end of the sorted list.

Every $p^{th}$ point is selected from the sorted list. In this way, more points are selected from similarity regions that are highly populated and fewer points are selected from sparsely populated regions. Selecting points in the manner described results in samples from each cluster that approximate the similarity distribution of the full data set. Similarity was determined using three different techniques and the results were compared. The three techniques are:

The hybrid angle-distance similarity technique; the Euclidian Distance technique; and the Anderson Darling statistic technique.

The hybrid angle-distance similarity measure is calculated as follows. The similarity, sim, between data vectors x and y each having dimension m is defined as follows. Let $$a_i = \frac{|x_i - y_i|}{r_i/\pi}$$

where $r_i$ is the range for the $i^{th}$ variable. We define the following variables:

$$d_x = \sqrt{\sum_i x_i^2}$$

$$d_y = \sqrt{\sum_i y_i^2}$$

$$d_{xy} = \sqrt{\sum_i (x_i - y_i)^2}$$

We calculate the variable sim, where $$sim = \frac{sim_a + sim_d}{m+1}$$

and $$sim_a = \sum_i \left(1 - \frac{a_i}{\pi}\right) = \sum_i \left(1 - \frac{|x_i - y_i|}{r_i/\pi}\frac{1}{\pi}\right) = \sum_i \left(1 - \frac{|x_i - y_i|}{r_i}\right)$$

$$sim_d = \begin{cases} 1 - \frac{d_{xy}}{d_x + d_y}, & d_x + d_y \neq 0 \\ 1, & d_x + d_y = 0 \end{cases}$$

The Euclidian Distance was also tested as a similarity measure. This is the distance of the vector from the cluster center.

$$d = \sqrt{\sum_i (x_i - y_i)^2}$$

where d is the distance, $x_i$ and $y_i$ are the $i^{th}$ elements of the vector and cluster center respectively.

The third measure of similarity tested was the Anderson-Darling test statistic, $A^2$. This is calculated using the formula presented earlier. In each case the cluster vectors were ordered according to their similarity values, and then representative vectors were selected as described above.

Comparative Results

A test matrix was devised, and tests were performed using combinations of the above described clustering and ordering techniques. Results were obtained for a variety of data. The test was performed as follows:

Training data was obtained for each model. From each data set we applied the selected combination of clustering and selection algorithms to obtain a reference matrix.

This reference matrix was used by an Expert State Estimation Engine (ESEE) multivariate kernel regression type predictive model implemented in the SURESENSE software product developed by Expert Microsystems of Orangevale, Calif., to determine predicted values for each vector in the original training data. The RMS error was calculated for each combination. A smaller RMS error indicates a better reduction and selection method.

RMS error is calculated as follows. Let $$errRMS_j = \sqrt{\frac{\sum_i (obs_{i,j} - pred_{i,j})^2}{n}}$$

$$obsRMS_j = \sqrt{\frac{\sum_i obs_{i,j}^2}{n}}$$

$$rmsRatio_j = \frac{errRMS_j}{obsRMS_j}$$

where j is the signal index, m is the total number of signals, i is the observation index, and n is the total number of observations.

$$RMSError\% = 100 \cdot \frac{\Sigma rmsRatio}{m}$$

$$StdDevRMSError\% = 100 \cdot \sqrt{\frac{\Sigma rmsRatio^2 - (\Sigma rmsRatio)^2/m}{m-1}}$$

FIG. 6 illustrates the research results for a variety of models and data sets. In nearly every case, the clustering method using the Anderson-Darling statistic for both clustering and ordering yields the lowest Mean RMS Error %. The exception is the Level Example test which yields a slightly better result for Anderson-Darling/Euclidian Distance. The results are comparable, so it appears that the best combination is the Anderson-Darling/Anderson-Darling combination.

Dynamic Data Filtering Procedure 34

Referring back to FIGS. 4 and 5, and in one embodiment, the dynamic data filtering procedure or method 34 is comprised of computer-executable instructions that, when executed by the processor 14, cause the processor 14 to perform the dynamic data filtering method 34, the method comprising the steps of: filtering acquired asset operating data values 32 or a transformation of the asset operating data values 32 for selectively choosing asset operating data values that meet at least one predefined criterion 62 of good data quality for defining good data 64 while rejecting asset operating data values that fail to meet at least the one predefined criterion 62 of good data quality for defining bad data 68; and storing the selectively chosen asset operating data values that meet at least the one predefined criterion 62 of good data quality or good data 64 for subsequent use in recalibrating at least one previously trained model 102 or recalibrated model 104 having a learned scope of normal operation of at least the one monitored asset 20 for adjusting the learned scope of at least the one previously trained model 102 or recalibrated model 104 for subsequent use with evolving asset operating data for determining or monitoring the condition of at least the one monitored asset 20.

Detailed Dynamic Data Filtering Procedure 34

Figure 4:
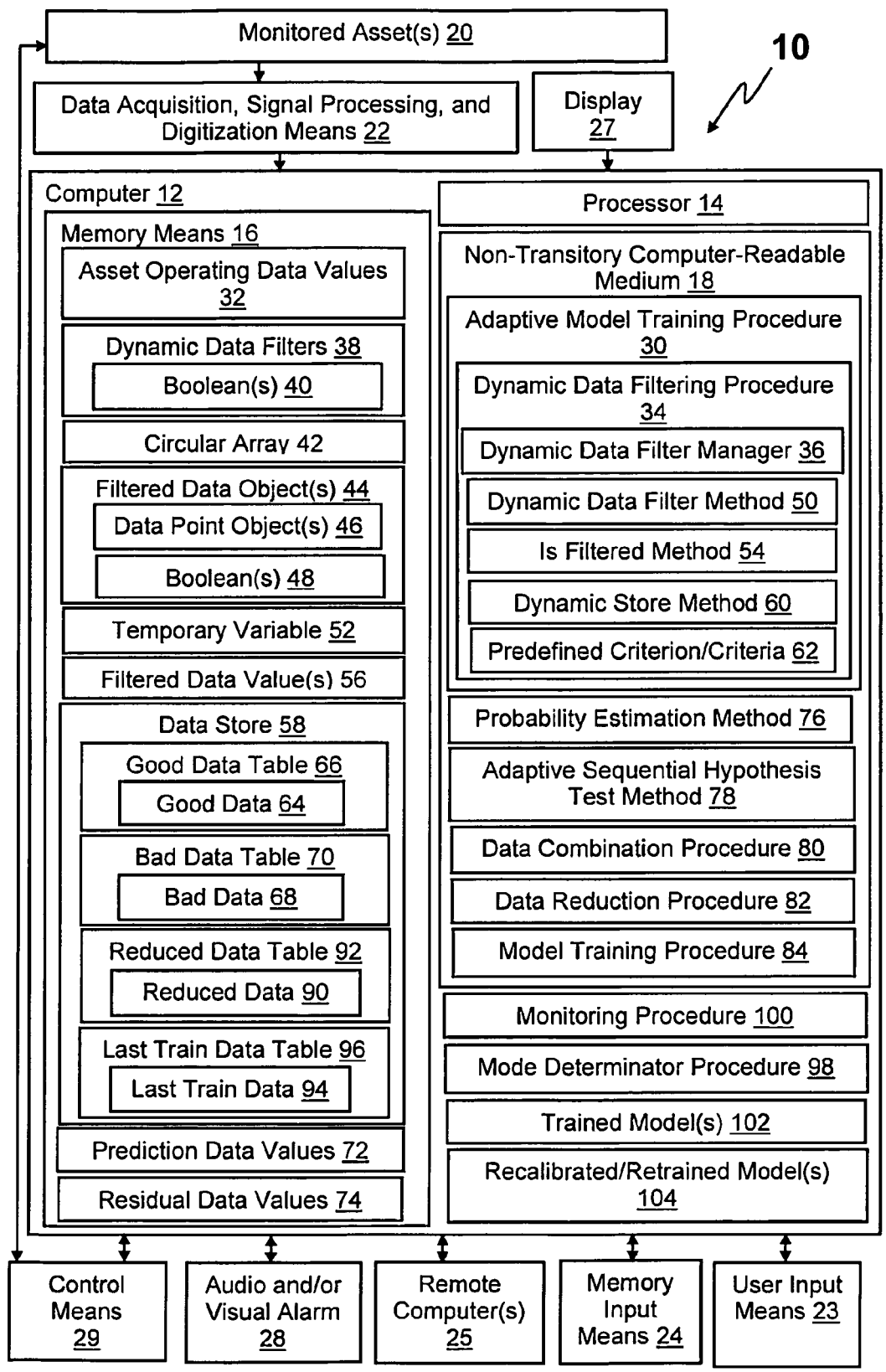
FIG. 4 is a functional block diagram of an embodiment of the adaptive model training system and method comprising a dynamic data filtering procedure or method.

More specifically, and still referring to FIGS. 4 and 5, an embodiment of the dynamic data filtering procedure or method 34 comprises a dynamic data filter manager (dynamicDataFilterManager) 36 comprised of a plurality of dynamic data filters (DynamicDataFilters) 38 and having a circular array 42 of length equal to the largest window size of any of its dynamic data filters (DynamicDataFilters) 38. Each element of the array 42 is a filtered data object (FilteredDataObject) 44 that contains a data point object (DataPoint) 46 having a data value such as one of the asset operating or observed data values 32 and a boolean 48 indicating whether or not the data point object (DataPoint) 46 should be filtered. When a dynamic data filter method (dynamicFilter(observation, prediction, residual)) 50 is called by the (dynamicDataFilterManager) 36, it will obtain the filtered data object (FilteredDataObject) 44 from the circular array 42 and assign it to a temporary variable 52. It will then call an is filtered method (is Filtered( ) 54 on each of the dynamic data filters (DynamicDataFilters) 38. Each of the dynamic data filters (DynamicDataFilters) 38 will return a boolean 40 indicating whether or not the filter failed. If failed is true, the manager will set each of the booleans 48 in the previous window_size-1 elements to true. The current data point object (DataPoint) 46 and filtering result or filtered data value 56 will be placed in the current filtered data object (FilteredDataObject) 44 location in the circular array 42. The filtered data object (FilteredDataObject) 44 stored in the temporary variable 52 is then returned and a pointer is advanced to the next data element. Notice that the return value contains a previous value, not the current observation. When the filtered data object (FilteredDataObject) 44 is returned, it passes to the data store (DataStore) 58 by way of a call to a dynamic store method (dynamicStore(FilteredDataObject)) 60. When the data store (DataStore) 58 receives the (FilteredDataObject) 44, it will store each of the filtered observation or data values 56 based on at least one predefined criterion 62 as a good data quality value 64 in a good data table (GoodData) 66 or it will store each of the filtered observation or data values 56 as bad data quality values 68 in a bad data table (BadData) 70 based on the value of the object's Boolean 48. This process continues for a user-specified period or on demand. At the end of this period or demand, the good data 64 can be utilized in the adaptive model training procedure 30 or other useful purpose.

The dynamic data filtering procedure or method 34 can also be utilized to filter prediction data values 72 and residual data values 74 in a manner analogues to that delineated above for the asset operating data or observed data values 32. Hence, the dynamic data filtering procedure or method 34 transforms asset operating data or observed data values 32, and/or prediction data values 72, and/or residual data values 74 into filtered data values 54 which are determined to be of a good or of a bad quality based on at least one predefined criterion 62 and which are respectively stored as good data 64 or bad data 68 based on the determination of quality.

Mathematical Description of Dynamic Data Filter Method 50

The dynamic data filter method 50 operates by determining whether an individual signal data value is "good" or "bad" based on one or more statistically based test methods of each of the asset operating data or observed data values 32, and/or prediction data values 72, and/or residual data values 74 in light of prior values and/or in light of data from other signals. Two such statistically based test methods providing at least one predefined criterion 62 are described below; however, the dynamic data filtering method 34 is not limited to the use of the following methods.

Probability Estimation Method 76

A Probability Estimation Method (PEM) 76 using Sequential Discounting Expectation Maximization (SDEM) was developed for use in the dynamic data filter method 50. This is an online discounting method providing a score to indicate the statistical outliers in a given collection of continuous valued data. This method has two characteristics:

First, the output is an aggregate score for every element of the observation array. And, second, the earlier observations are weighted less than the current observations.

A calibration or training method generates a Gaussian Mixture Model (GMM) that represents a probability density of the calibration or training data. The number of mixture components, k, is a user configurable variable.

For each calibration or training data point, x, the GMM is updated using SDEM which is described below. In the calibration or training step, the probability for each training point is estimated using the equations below.

$$p(x|\theta) = \sum_{i=1}^{k} w_i p(x|\mu_i, \Lambda_i)$$

$$p(x|\mu_i, \Lambda_i) = \frac{1}{(2\pi)^{n/2}|\Lambda_i|^{1/2}} \exp\left(-\frac{1}{2}(x-\mu_i)^T[(1-\lambda)(\Lambda_i + \varepsilon I)^{-1} + \lambda I](x-\mu_i)\right)$$

where k is the number of mixture components, each of which is assigned a weight $w_i$. Each mixture component defined in the second equation is an n dimensional Gaussian distribution with density specified by mean p, and covariance matrix $\Lambda_i$, where n is the number of continuous valued signals.

During data validation, a "score" is calculated. This is the shift in the probability density function if the current observation is added to the training data. The estimation process is as follows.

First, estimate the probability of the current observation vector given the current GMM using the equations above.

Second, update the GMM using SDEM and estimate the probability of the current observation vector using the updated GMM. Again, SDEM is described below.

Third, compute the probability density shift as the Hellinger distance between the current and the updated probability densities. This shift is output as the estimate generated by this method.

The SDEM method is a modified EM method. It comprises two steps:

First, the GMM parameters are initialized such that: Means ($\mu_{i0}$) are uniformly distributed over the data space; and Weights ($w_{i0}$) are set to 1/k.

And, second, the GMM parameters are updated using the following equations. The values for decay and $\alpha$ are preset default values set to 0.001 and 2.0, respectively. These default values have been found to produce reasonable results. The parameter decay is related to the degree of discounting for past examples. The parameter $\alpha$ is introduced in order to improve the stability of the estimates of $w_i$.

$$\gamma_i^{(t)} = (1 - \alpha * decay)\frac{w_i^{(t-1)}p(x_t|\mu_i^{(t-1)}, \Lambda_i^{(t-1)})}{\sum_{i=1}^{k} w_i^{(t-1)}p(x_t|\mu_i^{(t-1)}, \Lambda_i^{(t-1)})} + \frac{\alpha * decay}{k}$$

wherein,
$w_i(t) = (1-decay)w_i^{(t-1)} + decay*\gamma_i^{(t)}$
$\overline{\mu}_i^{(t)} = (1-decay)\overline{\mu}_i^{(t-1)} + decay*\gamma_i^{(t)}$
$\mu_i^{(t)} = \overline{\mu}_i^{(t)}/w_i^{(t)}$
$\overline{\Lambda}_i^{(t)} = (1-decay)\overline{\Lambda}_i^{(t-1)} + decay*\gamma_i^{(t)} \cdot x_t x_t^T$
and wherein, $$\Lambda_i^{(t)} = \frac{\overline{\Lambda}_i^{(t)}}{w_i^{(t)}} - \mu_i^{(t)}\mu_i^{(t)T}$$

The score is computed as the Hellinger distance ($d_h$) between the probability density ($p(.|\theta)$) of the training data and the updated probability density ($p(.|\theta')$) given the new observation vector.

$$Score = d_h\left(p(.|\theta), p(.|\theta')\square\sum_{i=1}^{k}\left(\sqrt{w_i} - \sqrt{w_i'}\right)^2 + \right.$$
$$\sum_{i=1}^{k}\frac{w_i + w_i'}{2}d_h(p(.|\mu_i, \Lambda_i), p(.|\mu_i', \Lambda_i'))$$

wherein,
$\theta = (w_i, \mu_i, \Lambda_i, \ldots w_k, \mu_k, \Lambda_k)$
and $$d_h(p(.|\mu_i, \Lambda_i), p(.|\mu_i', \Lambda_i')) =$$
$$\int \left(\sqrt{p(x|\mu_i, \Lambda_i)} - \sqrt{p(x|\mu_i', \Lambda_i')}\right)^2 dx = 2 - \frac{2|(\Lambda_i^{-1} + \Lambda_i'^{-1})/2|^{-\frac{1}{2}}}{|\Lambda_i|^{1/4}|\Lambda_i'|^{1/4}} \times$$
$$\exp[(1/2)(\Lambda_i^{-1}\mu_i + \Lambda_i'^{-1}\mu_i')^T(\Lambda_i^{-1} + \Lambda_i'^{-1})^{-1}(\Lambda_i^{-1}\mu_i + \Lambda_i'^{-1}\mu_i')] \times$$
$$\exp[-(1/2)(\mu_i^T\Lambda_i^{-1}\mu_i + \mu_i'^T\Lambda_i'^{-1}\mu_i')]$$

The results of the Probability Estimation Method or Predictive Model 76 can be used to determine whether the current observation is a statistical outlier. A limit threshold can be applied to the score and used to determine whether or not the observation is an outlier. An outlier would be determined to be bad data and a non-outlier would be determined to be good data thereby defining at least one predefined criterion 60.

Adaptive Sequential Hypothesis Test Method 78

Various estimation techniques are known to provide accurate estimates of sensor signals that can be used for on-line monitoring. The difference between a signal's predicted value and its directly sensed value or observed value is termed a residual. The residuals for each monitored signal are used as the indicator for sensor and equipment faults. Although simple thresholds could be used to detect fault indications (i.e., declaring a fault when a signal's residual value exceeds a preset threshold), we use a patented adaptive sequential probability (ASP) hypotheses test method 78 to determine whether the residual error value is uncharacteristic of the learned process model and thereby indicative of bad data, such as data arising from a sensor or equipment fault. The ASP hypotheses test method 78 improves the threshold detection process by providing more definitive information about signal validity using statistical hypothesis testing. The ASP hypotheses test method 78 allows the user to specify false alarm and missed alarm probabilities, allowing control over the likelihood of false alarms or missed detection. The ASP hypotheses test method 78 is a superior surveillance tool because it is sensitive not only to disturbances in the signal mean, but also to very subtle changes in the statistical quality (variance, skewness, bias) of the signals. For sudden, gross failures of an instrument or item of equipment, the ASP hypotheses test method 78 will annunciate the disturbance as fast as a conventional threshold limit check. However, for slow degradation, the ASP hypotheses test method 78 can detect the incipience or onset of the disturbance long before it would be apparent with conventional threshold limits. The ASP hypotheses test method 78 is described in U.S. Pat. No. 6,892,163; U.S. Pat. No. 7,082,379; and U.S. Pat. No. 7,158,917, which are all incorporated herein by reference in their entireties as though fully set forth herein and wherein each has a common inventor with the present application.

The ASP hypotheses test method 78 monitors successive observations of a process by analyzing the stochastic components of a short sequence of residuals using sequential hypothesis testing.

Let $Y_n$ represent the residual variable at a given moment $t_n$ in time where the sequence of recent values is given by $\{Y_n\} = \{y_1, y_2, \ldots y_n\}$. Let $H_0$ be a specific probability density function (PDF) called the null hypothesis. The probability that the time series $\{Y_n\}$ contains samples drawn from $H_0$ is $P(y_1, y_2, \ldots, y_n|J_0)$. Let $H_j$ be a different probability density function called the alternative hypothesis. The probability that the time series $\{Y_n\}$ contains samples drawn from $H_j$ is $P(y_1, y_2, \ldots y_n|H_j)$. Two threshold limits A and B are chosen, with A<B, and for each observation in the series the following statistic ($\Lambda_{j,n}$) is calculated:

$$\Lambda_{j,n} = \prod_{i=1}^{n}\frac{P(y_i|H_j)}{P(y_i|H_0)}.$$

The test procedure is then as follows. If the statistic is greater than or equal to the upper threshold limit (i.e., $\Lambda_{j,n} \geq B$), then a decision is made to accept hypothesis $H_j$ as true. If the statistic is less than or equal to the lower threshold limit (i.e., $\Lambda_{j,n} \leq A$), then a decision is made to accept hypothesis $H_0$ as true. If the statistic falls between the two limits (i.e., A<
$\Lambda_{j,n}$<B), then neither hypothesis can yet be accepted to be true
and sampling continues. The ASP hypotheses test method 76
allows the user to specify the targeted likelihood of missed
detection or false alarm. The threshold limits are related to the
misidentification probabilities as follows:

$$A = \frac{\beta}{1-\alpha}$$
and
$$B = \frac{1-\beta}{\alpha}$$

wherein $\alpha$ is the false alarm probability of accepting $H_j$ when
$H_0$ is true and $\beta$ is the missed detection probability of accepting $H_0$ when $H_j$ is true.

The ASP hypotheses test method 78 broadens the domain
of applicability of the hypothesis test to encompass non-
Gaussian probability density functions. In the ASP hypotheses test method 78, the requirement that the data fit a Gaussian probability density function is relaxed and the test
statistic is evaluated for any arbitrary data distribution. In the
ASP hypotheses test method 78, the residual is assumed to
consist of random observations that adhere to a general probability density function, $\Im(y; \mu, \sigma^2, \dots)$, of the sample mean,
variance, and higher order terms, such as the skewness, or
kurtosis. This is important because real-world residual distributions have "fatter tails" than a Gaussian distribution and the
higher probability mass in the tails is a prime cause of false
alarms using a sequential probability ratio test (SPRT) or
threshold methods.

The ASP hypotheses test method 78 is accomplished by
first establishing the expected distribution of the residual
values when the system is operating normally. The ASP
hypotheses test method 78 numerically fits a probability density function to the residuals. In one embodiment, our
approach also includes a Bayesian conditional probability
filter used as a post-processing element of the ASP hypotheses test method 78 to suppress single observation false
alarms due to occasional data outliers. The method examines
the series of decisions reported by an ASP fault detection test
to determine the probability that the series supports the alternative hypothesis, $H_j$. Each decision in the series is treated as
a piece of evidence and Bayes' rule is used to update the
conditional probability of the alternative hypothesis based on
that evidence. When the conditional probability becomes
large, the method will conclude that a true fault has occurred.

Attributes of the Dynamic Data Filtering Procedure 34

In one embodiment, the dynamic data filtering procedure
or method 34 has the following attributes:

Dynamic data filters operate during on-line or periodic
monitoring.

Dynamic data filters operate on observed, predicted and/or
residual data.

Dynamic data filters can be trainable versions of statistical
fault detectors used to perform on-line monitoring fault
detection.

Any statistical fault detector method can be used as a
dynamic data filter, such as a threshold comparison test or a
sequential hypothesis test as delineated above.

Dynamic data filters can themselves be calibrated during
initial static model training and optionally during dynamic
model training using the dynamically filtered data.

Dynamic data filters can operate on an individual signal or
on groups of signals, accepting or rejecting the group of data
based on attributes of one or more of the signals in the group.
For example, a RMS data filter might operate on a group of
residual signals and calculate the overall root mean squared
(RMS) value. If the RMS value exceeds a threshold, the
dynamic data filter rejects all data within the observation
group.

In one embodiment, and in addition to determining the
goodness of a new observation, the method 34 can also determine the goodness of data as a whole. If the newly observed
data is generally bad, adaptive calibration of the model 102 or
104 should not be performed using the data even if some of
the individual observations pass the filtering process. More
specifically, take an example were a signal drifts out of range.
Even though the signal has basically failed, a small number of
observations might be deemed good due to random signal
noise. In this case, none of the data should be used for training
as the good data is only a consequence of the noise in the
signal. In one embodiment, a measure of the proportion of
good data obtained during monitoring is used to determine
the goodness of data as a whole. If 100,000 observations have
been monitored, and 95,000 observations passed the filtering
process, then the overall measure of goodness is 0.95. The
threshold value for performing adaptive calibration of the
model 102 or 104 using this metric is often a configurable
threshold value. Accordingly, an overall measure of goodness
can be obtained by computing a ratio of the number of good
data quality values in a set of filtered data values to the sum of
the number of both the good data quality values and the bad
data quality values in the set for defining the overall measure
of goodness that can be compared to a configurable threshold
value for performing the adaptive model training procedure
30 of the model 102 or 104.

In Use and Operation

Figure 7:
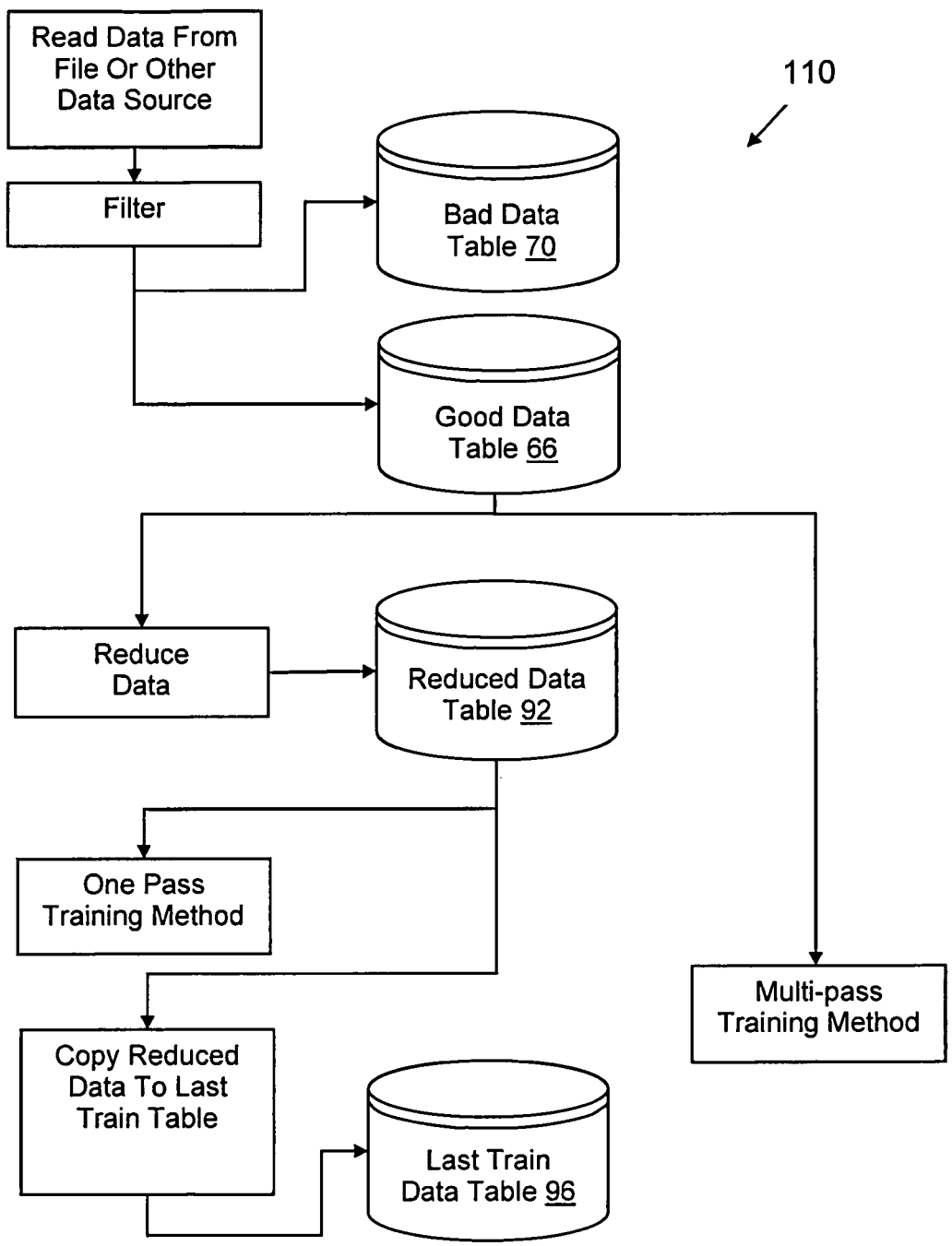
FIG. 7 is a data flow diagram of an embodiment of a static training procedure or method of a model representative of normal operation of at least one monitored asset.

In use and operation, and before the adaptive model training procedure 30 begins, a static training method 110 begins
as outlined in FIG. 7 and before the static training method 110
begins, four tables (FIGS. 1 and 4) are established for each
phase (operating mode) in each model 102, the good data
table 66, the bad data table 70, a reduced data table 92, and a
last train data table 96. Then, the data flow of the static
training method 110 proceeds as follows: Corresponding to
each determined phase, obtain data from files or other data
source. Filter the data and store it in the good data table 66 and
the bad data table 70 as appropriate. Reduce the data from the
good data table 66 and store it in the reduced data table 92.
Obtain the data from the reduced data table 92 and train using
a one pass training method or procedure 86 (FIG. 1) of the
model training method or procedure 84 or obtain the data 64
from the good data table 66 and train using a multiple pass
training method or procedure 88 (FIG. 1) of the model training procedure 84. Copy the reduced data 90 from the reduced
data table 92 to the last train data table 96. This process is
repeated in succession or simultaneously for each phase (operating mode) in each model 102 that is calibrated or trained.

Figure 8:
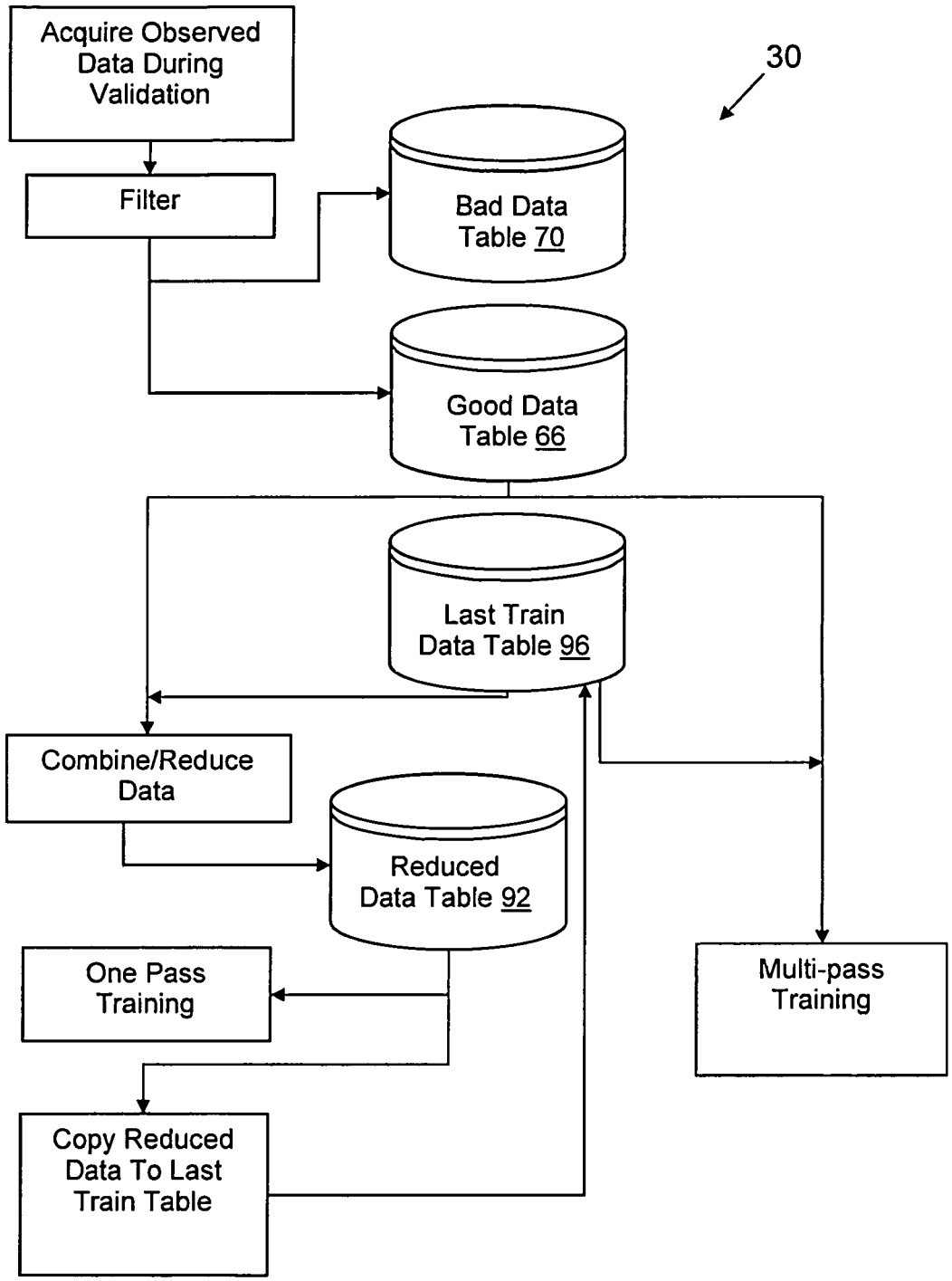
FIG. 8 is a data flow diagram of an embodiment of an adaptive model training procedure or method of a model representative of normal operation of at least one monitored asset.

Now, an outline of an embodiment of data flow of the
adaptive model training procedure 30 is illustrated in FIG. 8
and proceeds as follows: Acquire asset operating or observed
data values 32 and phase (operating mode) during validation
of data during the monitoring procedure 100. Filter the asset
operating data values 32 and store them in the good data table
66 and the bad data table 70 as delineated hereinabove. Combine and optionally reduce the data from the last train data
table 96 and the good data table 66 and store it in the reduced
data table 92. Obtain the data from the reduced data table 92
and train using the one pass training method 86 of the model
training procedure 84 and/or obtain the data from the last train
data table 96 and good data table 66 and train using the multiple pass training method 88 of the model training procedure 84. Copy the data from the reduced data table 92 to the last train data table 96.

In-Service Application: Operation and Use

In this work for the U.S. Department of Energy, a model 102 was built based on four feedwater level signals CP-01, CP-02, CP-03, and CP-04 from a monitored asset 20 in the form of, but not limited to, a steam generator in an operating nuclear power plant. The signals incorporated into the model are listed in the table illustrated in FIG. 9.

Figure 10:
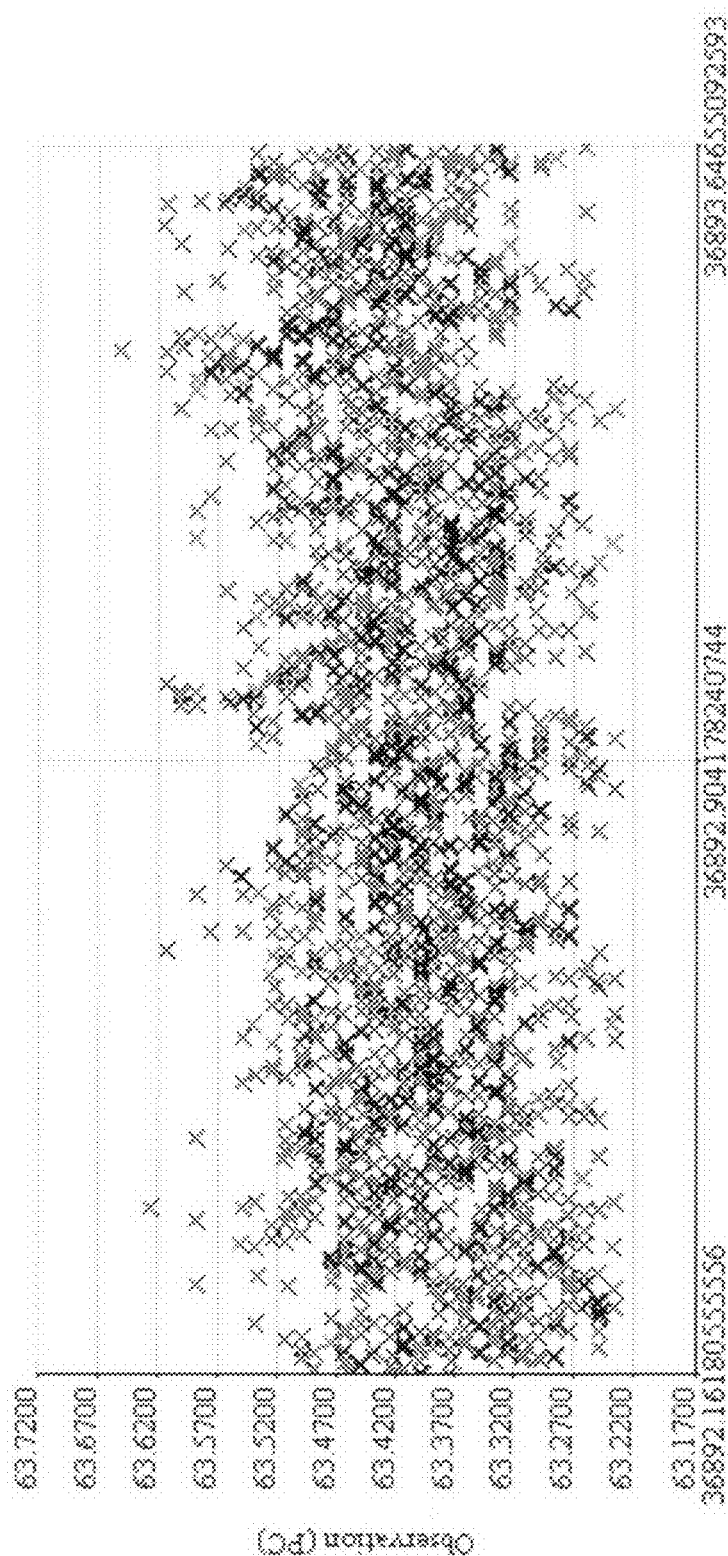
FIG. 10 is a plot of original training data obtained from sensor signal CP-01 categorized in the table illustrated in FIG. 9.

The model was built utilizing the SURESENSE software product including the ESEE empirical predictive model and developed by Expert Microsystems of Orangevale, Calif., 95662-2120; (916) 989-2018. Evaluation Data FIG. 10 illustrates a plot of original training data obtained from sensor signal CP-01 categorized in the table illustrated in FIG. 9. Using a Signal Simulator we simulated the original training data to create a simulated data set containing 77760 points sampled at 6 points per hour. This simulated data is representative of 18 months of feedwater level sensor data.

Figure 11:
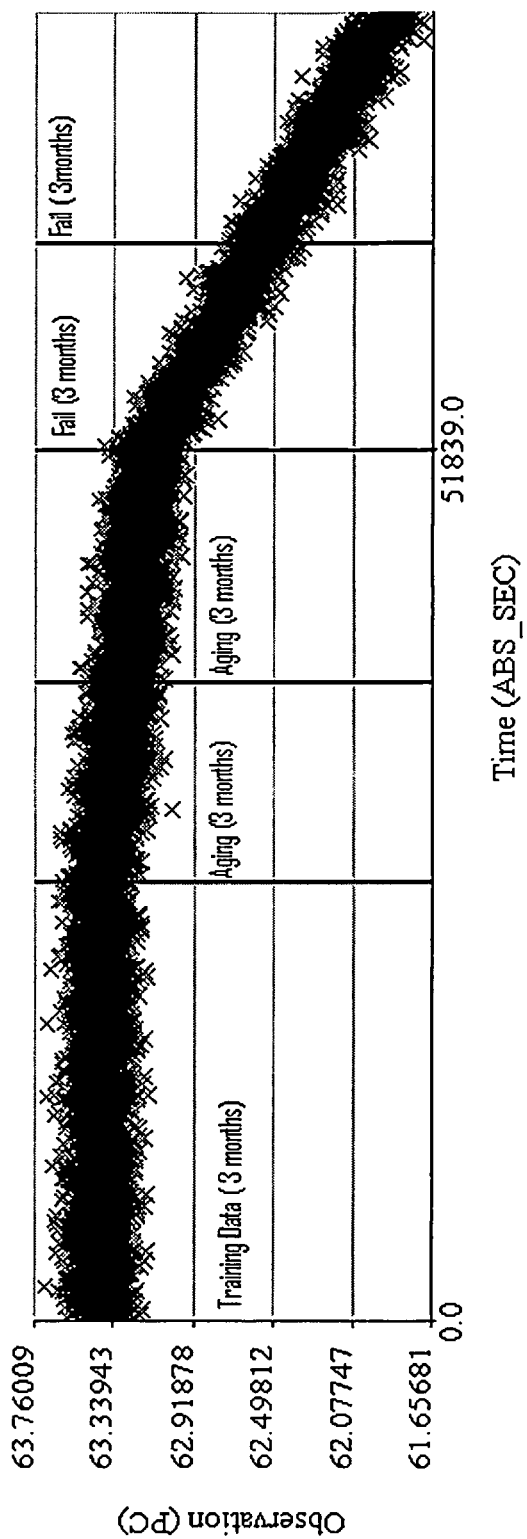
FIG. 11 is a plot of a simulated data set of the original training data obtained from sensor signal CP-01 with aging and failure data introduced therein.
Figure 12:
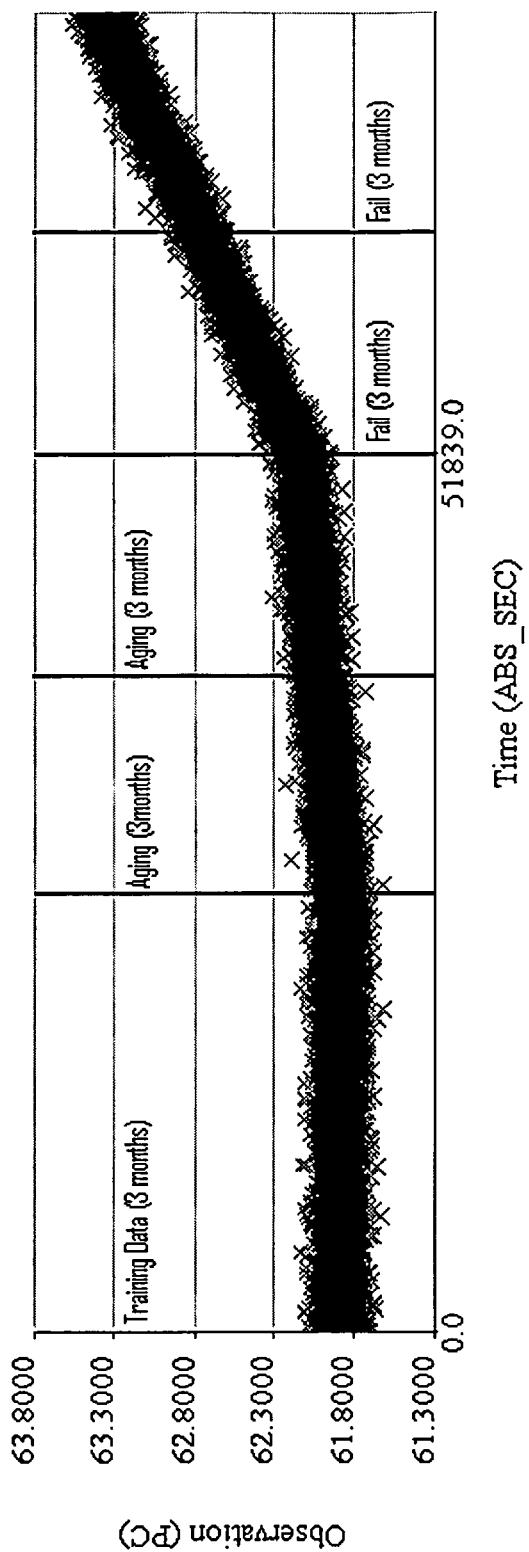
FIG. 12 is a plot of a simulated data set of the original training data obtained from sensor signal CP-03 with aging and failure introduced therein.

Aging and Failure were introduced in the simulated data as shown in FIG. 11 and FIG. 12. Aging was introduced at the end of six months of simulated training data (25920 data points). The onset of sensor failure was introduced at the end of six months of aging (51840 data points) and continued till the end of the 18 month period. Aging and Failure were introduced in the data for the CP-01 and CP-03 sensors only. Aging was introduced such that the total drift in six months of aging equals 0.25% of the level sensor span (0.25 PCT). Failure was introduced such that the total drift in six months of failure equals 1.5% of the level sensor span (1.5 PCT).

Predictive Model

An ESEE empirical predictive model was used as model 102 to model the steam generator feedwater levels. CP-01, CP-02, CP-03, and CP-04 are used as inputs to the predictive model. A reference matrix of 35 vectors was selected. The ESEE clustering parameter was set to 0.8

Fault Detectors

Gaussian Mean type ASP fault detectors provided in the SURESENSE software were applied to all residual signals generated using the ESEE predictive model. The disturbance magnitude for each fault detector was set to 10. The multi-cycle event filter window size was set to 10 to provide false alarm filtering.

Dynamic Data Filters

Gaussian Mean type ASP dynamic data filters were applied to all residual signals generated using the ESEE predictive model. The disturbance magnitude was set to 15. The multi-cycle event filter window size was set to 1 to ensure that all outliers are rejected by the dynamic data filter. The dynamic data filter disturbance magnitude was set higher than the fault detector disturbance magnitude to allow the model to adapt to aging but not so high as to allow the model to learn failure data.

Test Results

The model was trained with the training data contained in the first six months of the simulated data.

The model was run with the first three months of aging data (12951 data points or values). The dynamic data filters identified 9 outliers in the 12951 data points. The data quality index evaluated to 99.93% which is greater than the minimum required data quality of 75%. Therefore the model made a determination to update its training using this first three months of aging data.

Next, the model was run with the last three months of aging data (12951 data points). The dynamic data filters identified 19 outliers in the 12951 data points. The data quality index evaluated to 99.85% which is greater than the minimum required data quality of 75%. Therefore the model made a determination to update its training using this last three months of aging data.

The model was run with the first three months of failure data (12951 data points). The dynamic data filters identified 8538 outliers in the 12951 data points. The data quality index evaluated to 34.07% which is less than the minimum required data quality of 75%. Therefore the model made a determination not to update its training using this first three months of failure data.

Next, the model was run with the last three months of failure data (12951 data points). The dynamic data filters identified 12951 outliers in the 12951 data points. The data quality index evaluated to 0% which is less than the minimum required data quality of 75%. Therefore the model made a determination not to update its training using this first three months of failure data.

In summary, dynamic data filtering in combination with adaptive (dynamic) model training enabled the model to adapt to aging and simultaneously reject failure data.

Model Performance Comparisons with and without Adaptive Training

Model Performance with Adaptive Training Disabled

The model was trained on the simulated six months of training data. This model was run with the aging and failure data without dynamic data filtering and adaptive model training. This model did not generate any false alarms on the first three months of aging data. However, the model generated 4,012 false alarms on sensor CP-01 and 2225 false alarms on sensor CP-03 on the last three months of aging data. The onset of failure on sensor CP-01 in the first three months of failure was detected after 53,157 data points. The onset of failure on sensor CP-03 in the first three months of failure was detected after 52,469 data points. However, the failure was instantly detected for the last three months of failure. The detection time for the failure data of sensor CP-01 was 1,317 seconds and the detection time for the failure data of sensor CP-03 was 629 seconds.

Model Performance with Adaptive Training Enabled

The model was trained on the simulated six months of training data. This model was run with the first three months of aging data with dynamic data filtering and adaptive model training enabled. The model adapted to the aging and was then run with the last three months of aging and failure data without adaptive training. It was observed that the model generated 108 false alarms on the CP-01 sensor for the last three months of the aging data. Thus, the number of false alarms is greatly reduced by adaptive training over the first three months of aging. The onset of failure on sensor CP-01 in the first three months of failure was detected after 53,346 data points. The onset of failure on sensor CP-03 in the first three months of failure was detected after 56,214 data points. However, the failure was instantly detected for the last three months of failure. The detection time for the failure data of sensor CP-01 was 1,506 seconds and the detection time for the failure data of sensor CP-03 was 4,284 seconds. Comparing the failure times with adaptive trainin g disabled and with dynamic data filtering and adaptive model training enabled indicates that the failure detection time is slightly delayed with the adaptive training enabled because of adaptive training over the first three months of aging.

Next, the model was run with the last three months of aging data with dynamic data filtering and adaptive model training enabled. The model adapted to the last three months of aging data and was then run with the failure data without adaptive training. It was observed that the model did not generate any false alarms on aging data, since it adapted to the aging data. Thus, the number of false alarms is eliminated by adaptive training over the last three months of aging. The onset of failure on sensor CP-01 in the first three months of failure was detected after 56,460 data points. The onset of failure on sensor CP-03 in the first three months of failure was detected after 56,124 data points. However, the failure was instantly detected for the last three months of failure. The detection time for the failure data of sensor CP-01 was 4,620 seconds and the detection time for the failure data of sensor CP-03 was 5,769 seconds. Comparing the failure times with adaptive trainin g disabled and with dynamic data filtering and adaptive model training enabled indicates that the failure detection time is slightly delayed because of adaptive training over the last three months of aging.

In summary, adaptive (dynamic) model training enabled the model to adapt to aging, thus reducing the false alarms on the aging data. However, this delays the detection of the onset of sensor failure by a small amount.

Summary of Benefits

The adaptive model training system and method 10 enables the rapid, cost effective deployment of Asset Performance Management (APM) systems for a wide variety of valuable commercial applications, including power plants, military and aerospace systems, and other performance and safety critical assets. With respect to provided benefits, the system and method 10 supports the DOE's objective to ensure the continued safe and reliable operation of this nation's nuclear power plants. The system and method 10 enables improved modeling software that uses innovative artificial intelligence techniques to (1) ensure the accurate measurement of key reactor and plant parameters (data validation), (2) assess equipment in-service performance (on-line condition monitoring and instrument calibration reduction), and (3) determine equipment integrity and the need for maintenance (condition-based maintenance). The system and method 10 additionally supports nuclear power industry goals of >99% plant availability and to reliability program directives for "zero tolerance" of unanticipated equipment failures. System and method 10 goes beyond the Maintenance Rule (10 CFR 50.65) guidelines, which focus on equipment failures, by providing the means to detect equipment degradation prior to a failure with improved confidence.

The above delineation of the adaptive model training system and method 10, including its use and operation, demonstrates the industrial applicability of this invention.

Moreover, it should be apparent that numerous modifications and adaptations may be resorted to without departing from the scope and fair meaning of the instant invention as set forth hereinabove and as described herein below by the claims.

We claim:

1. A computer-implemented adaptive model training method, said method comprising the steps of:
   providing a previously trained model having a learned scope of normal operation of an asset obtained from an initial set of training data values;
   acquiring a set of asset operating data values from the asset for defining operation of the asset;
   assigning a measure of data quality to the asset operating data values in the acquired set of asset operating data values based on at least one predefined criterion for comparing the asset operating data values in the acquired set of asset operating data values with the previously trained model having the learned scope of normal operation of the asset;
   filtering the acquired set of asset operating data values for selecting an additional set of training data values from the acquired set of asset operating data values based on at least one predefined criterion of good data quality utilizing the measure of data quality assigned to the asset operating data values in the acquired set of asset operating data values;
   creating an adapted set of training data values for defining an adapted scope of normal operation of the asset by combining at least one of the data values from the initial set of training data values with at least one of the data values from the selected additional set of training data values based on at least one predefined criterion for selectively choosing the data values included in the adapted set of training data values; and
   recalibrating the previously trained model having the learned scope of normal operation of the asset by utilizing the created adapted set of training data values for adjusting the learned scope of normal operation of the asset for defining a recalibrated model having the adjusted learned scope of normal operation of the asset.

2. The computer-implemented method of claim 1 further comprising the steps of:
   subsequently filtering subsequently acquired asset operating data values from the asset for selectively choosing subsequently acquired asset operating data values that meet at least the one predefined criterion of good data quality while rejecting subsequently acquired asset operating data values that fail to meet at least the one predefined criterion of good data quality; and
   subsequently recalibrating the recalibrated model having the adjusted learned scope of normal operation of the asset by utilizing the subsequently acquired asset operating data values that meet at least the one predefined criterion of good data quality for subsequently adjusting the learned scope of normal operation of the asset.

3. The computer-implemented method of claim 2 further comprising a step of iteratively repeating the subsequently filtering step followed by the subsequently recalibrating step as a function of a user-specified period.

4. The computer-implemented method of claim 2 further comprising a step of iteratively repeating the subsequently filtering step followed by the subsequently recalibrating step as a function of user demand.

5. A non-transitory computer-readable medium containing computer-executable instructions that, when executed by a processor, cause the processor to perform an adaptive model training method, said method comprising:
   providing a previously trained model having a learned scope of normal operation of an asset obtained from an initial set of training data values;
   acquiring a set of asset operating data values from the asset for defining operation of the asset;
   assigning a measure of data quality to the asset operating data values in the acquired set of asset operating data values based on at least one predefined criterion for comparing the asset operating data values in the acquired set of asset operating data values with the previously trained model having the learned scope of normal operation of the asset;
   filtering the acquired set of asset operating data values for selecting an additional set of training data values from the acquired set of asset operating data values based on at least one predefined criterion of good data quality utilizing the measure of data quality assigned to the asset operating data values in the acquired set of asset operating data values;

creating an adapted set of training data values for defining an adapted scope of normal operation of the asset by combining at least one of the data values from the initial set of training data values with at least one of the data values from the selected additional set of training data values based on at least one predefined criterion for selectively choosing the data values included in the adapted set of training data values; and recalibrating the previously trained model having the learned scope of normal operation of the asset by utilizing the created adapted set of training data values for adjusting the learned scope of normal operation of the asset for defining a recalibrated model having the adjusted learned scope of normal operation of the asset.

6. The non-transitory computer-readable medium of claim 5 further comprising the steps of:

subsequently filtering subsequently acquired asset operating data values from the asset for selectively choosing subsequently acquired asset operating data values that meet at least the one predefined criterion of good data quality while rejecting subsequently acquired asset operating data values that fail to meet at least the one predefined criterion of good data quality; and subsequently recalibrating the recalibrated model having the adjusted learned scope of normal operation of the asset by utilizing the subsequently acquired asset operating data values that meet at least the one predefined criterion of good data quality for subsequently adjusting the learned scope of normal operation of the asset.

7. The non-transitory computer-readable medium of claim 6 further comprising a step of iteratively repeating the subsequently filtering step followed by the subsequently recalibrating step as a function of a user-specified period.

8. The non-transitory computer-readable medium of claim 6 further comprising a step of iteratively repeating the subsequently filtering step followed by the subsequently recalibrating step as a function of user demand.

9. An adaptive model training system, said system comprising:

a previously trained model stored in a non-transitory computer-readable medium, said previously trained model having a learned scope of normal operation of the asset;

means for acquiring a set of asset operating data values from the asset for defining operation of the asset;

assigning a measure of data quality to the asset operating data values in the acquired set of asset operating data values based on at least one predefined criterion for comparing the asset operating data values in the acquired set of asset operating data values with the previously trained model having the learned scope of normal operation of the asset;

means for filtering the acquired set of asset operating data values for selecting an additional set of training data values from the acquired set of asset operating data values based on at least one predefined criterion of good data quality utilizing the measure of data quality assigned to the asset operating data values in the acquired set of asset operating data values;

means for creating an adapted set of training data values for defining an adapted scope of normal operation of the asset by combining at least one of the data values from the initial set of training data values with at least one of the data values from the selected additional set of training data values based on at least one predefined criterion for selectively choosing the data values included in the adapted set of training data values; and means for recalibrating the previously trained model having the learned scope of normal operation of the asset by utilizing the created adapted set of training data values for adjusting the learned scope of normal operation of the asset for defining a recalibrated model having the adjusted learned scope of normal operation of the asset.

10. The system of claim 9 further comprising:

means for subsequently filtering subsequently acquired asset operating data values from the asset for selectively choosing subsequently acquired asset operating data values that meet at least the one predefined criterion of good data quality while rejecting subsequently acquired asset operating data values that fail to meet at least said one predefined criterion of good data quality; and means for subsequently recalibrating said recalibrated model having said learned scope of normal operation of the asset by utilizing the subsequently acquired asset operating data values that meet at least said one predefined criterion of good data quality for readjusting said learned scope of normal operation of the asset for defining a subsequently recalibrated model having said readjusted learned scope of normal operation of the asset.

11. The system of claim 9 further comprising means for iteratively repeating said subsequently filtering function followed by the subsequently recalibrating function based on a user-specified period.

12. The system of claim 9 further comprising means for iteratively repeating said subsequently filtering function followed by said subsequently recalibrating function based on user demand.

13. A computer-implemented adaptive model training method, said method comprising the steps of:

providing an initial set of training data values;

calibrating a model for defining an initial scope of normal operation of an asset using the provided initial set of training data values;

acquiring an additional set of data values from the asset for defining operation of the asset;

assigning a measure of data quality to the data values in the acquired additional set of data values based on at least one predefined criterion for comparing the data values in the acquired additional set of data values with the model for defining the scope of normal operation of the asset;

selecting an additional set of training data values from the acquired additional set of data values based on at least one predefined criterion of good data quality using the measure of data quality assigned to the data values in the acquired additional set of data values;

creating an adapted set of training data values for defining an adapted scope of normal operation of the asset by combining at least one of data values from the provided initial set of training data values with at least one of the data values from the selected additional set of training data values based on at least one predefined criterion for selectively choosing the data values included in the adapted set of training data values; and recalibrating the model for defining the scope of normal operation of the asset using the created adapted set of data values for defining a recalibrated model having an adjusted scope of normal operation of the asset.

14. The computer-implemented method of claim 13 further comprising the steps of:

acquiring a further set of data values for defining an operation of the asset;

assigning a measure of data quality to the data values in the acquired further set of data values based on at least one predefined criterion for comparing the data values in the acquired further set of data values with the recalibrated model for defining the scope of normal operation of the asset;

selecting a further set of training data values from the acquired further set of data values based on at least one predefined criterion using the measure of data quality assigned to the data values in the acquired further set of data values;

creating a further adapted set of training data values for defining a further adapted scope of normal operation of the asset by combining at least one of data values from the created adapted set of data values with at least one of the data values from the selected further set of training data values based on at least one predefined criterion for selectively choosing the data values included in the further adapted set of training data values;

recalibrating the recalibrated model for defining the scope of normal operation of the asset using the created further adapted set of training data values.

15. The computer-implemented method of claim 13 wherein the step of assigning a measure of data quality to the data values in the acquired additional set of data values includes the steps of:

estimating the expected value of at least one data value in the acquired additional set of data values using the model for defining the scope of normal operation of the asset;

comparing at least one data value in the acquired additional set of data values with the estimated expected value of at least one data value in the acquired additional set of data values;

assigning a measure of data quality to the data values in the acquired additional set of data values based on the comparing step.

* * * * *